United States Patent [19]
Ogura et al.

[11] Patent Number: 4,489,211
[45] Date of Patent: Dec. 18, 1984

[54] PROCESS FOR PRODUCING 2,2,2-TRIFLUOROETHANOL

[75] Inventors: Eiji Ogura; Kunihiro Mito; Shoji Arai, all of Sinnanyo, Japan

[73] Assignees: Onoda Cement Co., Ltd., Onoda; Toyo Soda Manufacturing Co., Ltd., Shinnanyo, both of Japan

[21] Appl. No.: 463,019

[22] Filed: Feb. 1, 1983

[30] Foreign Application Priority Data

Feb. 4, 1982 [JP] Japan .................................. 57-16821
Feb. 9, 1982 [JP] Japan .................................. 57-19493

[51] Int. Cl.³ ........................ C07C 31/34; C07C 29/09
[52] U.S. Cl. ..................................... 568/842; 570/137
[58] Field of Search ......................... 568/842; 570/137

[56] References Cited

U.S. PATENT DOCUMENTS 4,001,309  1/1977  Hayashi et al. ..................... 568/842
4,219,681  8/1980  Schweak et al. .................... 568/842
4,359,371  11/1982  Bohm et al. ........................ 568/842

OTHER PUBLICATIONS

McBee et al.; J. Am. Chem. Soc., vol. 84, 1962, pp. 3157–3160.
Riddick et al.; Organic Solvents, vol. II, Weissberger, Techniques of Organic Chemistry, Third Edition, pp. 836, 837, 848, and 849.
Lederer, C.A. 69, 1968, 51575y, Czech. 124981, Nov. 15, 1967.
Perry et al., Techniques of Chemistry, vol. XII, Separation and Purification, John Wiley & Sons, New York (1978), pp. 50–55.

Primary Examiner—Howard T. Mars
Attorney, Agent, or Firm—Oblon, Fisher, Spivak, McClelland & Maier

[57] ABSTRACT

A process for producing 2,2,2-trifluoroethanol, which is used for modifying inorganic high polymers such as phosphazene polymers being thermo-resistant, inflammable and oil-resistant, by employing γ-butyrolactone as a reaction solvent.

6 Claims, No Drawings

PROCESS FOR PRODUCING 2,2,2-TRIFLUOROETHANOL

DETAILED DESCRIPTION OF THE INVENTION 2,2,2-trifluoroethanol has a OH group showing a weak acidity and is an extremely thermo-stable fluorine-containing alcohol. For these reason, it is used for modifying inorganic high polymers such as phosphazene polymers which are thermo-resistant, flexible in a low temperature, inflammable and oil-resistant.

On the other hand, investigations for saving energy have recently proceeded and 2,2,2-trifluoroethanol is used as a processing medium in electric generation systems ("organic ranking cycle system") for recovering waste heats which are in medium or low temperature ranges (200°~500° C.) and exhausted from various production installations, and waste heats from large scale Diesel engines.

Heretofore, it has been known as a process for producing this alcohol, reduction of an ester of trifluoroacetic acid by LiAlH$_4$ (J. Am. Chem. Soc., 1968 (1948)) or a process by derivating it from 1,1,1-trifluoro-2-chloroethane. However, because LiAlH$_4$ is highly costful the reduction of the ester of trifluoroacetic acid is industrially not practical.

It has been known as the process of derivation from 1,1,1-trifluoro-2-chloroethane on in which it is reacted by fusing it with sodium acetate or it is reacted with sodium acetate in acetic acid used as a solvent. However, the yield depends on the reaction temperature in these reactions and therefore it is inevitable to carry out the reaction for a considerably long time when an improved yield is sought. In addition, the process is accompanied with a complication that the resulting product is 2,2,2-trifluoroethyl acetate which should be subjected to a further additional step of hydrolysis.

There is described a process in U.S. Pat. No. 2,868,846, in which CF$_3$CH$_2$Cl is reacted with an alkali metal salt in a solvent having hydroxyl groups, such as ethyleneglycol to produce the object product. However, it hardly seems that this process is satisfactory one as an industrial production process because the reaction temperature is high to cause a thermal degradation of glycols consisting the solvent, a corrosion of structural materials of the reaction vessel and further to result in an occurrence of side-reactions and so on with the product formation.

The inventors have diligently conducted investigations as to processes for producing 2,2,2-trifluoroethanol from a 1,1,1-trifluoro-2-halogenated ethane (CF$_3$CH$_2$X, wherein X is Cl or Br) and as a result, found that this reaction can be effected under moderate conditions when it is conducted by using γ-butyrolactone as the solvent. This finding leads the inventors to the present invention.

Namely, this invention provides a process for producing 2,2,2-trifluoroethanol, in which 1,1,1-trifluoro-2-halogenated ethane is reacted in γ-butyrolactone used as a solvent in the presence of one member or not less than two members of the several reagent systems (a) to (e)

(a) water and at least one class of carboxylic acid salt represented by the general formula

RCOOM wherein R is an alkyl group or a hydroxyalkyl group, each of which has a carbon number of not more than 19, or phenyl group, and M is Na, K or Mg;

(b) water and at least one class of dicarboxylic acid salt represented by the general formula

MOOCR'COOM' wherein R' is an alkylene group having a carbon number of 0 to 8, or phenylene group, and M and M' are Na, K or Mg, which can be identical to or different from each other;

(c) water and at least one class of dicarboxylic acid salt having an ether-bonding in molecule, which is represented by the general formula

MOOCR'OR"COOM' wherein R' and R" are alkylene groups having a summed up carbon number of not more than 10, which can be identical to or different from each other, and M and M' are Na, K or Mg, which can be identical to or different from each other;

(d) water and at least one class of alkalline substances consisting of NaOH, KOH, Na$_2$CO$_3$, K$_2$CO$_3$, NaHCO$_3$ and KHCO$_3$; and (e) at least one class of salts of hydroxy-carboxylic acids represented by the general formula

R'"COOM wherein R'" is a hydroxy alkyl group having a carbon number of not more than 5, and M is Na, K or Mg.

DETAILS OF THIS INVENTION IS EXPLAINED HEREIN-BELOW

The reaction of this invention is carried out in a pressure-vessel.

The 1,1,1-trifluoro-2-halogenated ethane is 1,1,1-trifluoro-2-chloroethane or 1,1,1-trifluoro-2-bromoethane as appearing in the above formula.

There are various processes as ones for producing 1,1,1-trifluoro-2-bromoethane but a new process invented by the present inventor is excellent, in which 1,1,1-trifluoroethane and bromine are reacted in the presence of chlorine to give 1,1,1-trifluoro-2-bromoethane.

The process follows to the below-stated reaction-equation, in which the conversion of bromine is large and moreover, the production of chlorine-containing compounds is in an extremely small amount.

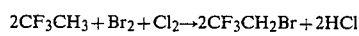

$$2CF_3CH_3 + Br_2 + Cl_2 \rightarrow 2CF_3CH_2Br + 2HCl$$

The reaction temperature ranges 400° to 800° C., preferably 500° to 750° C. The mixture ratio of bromine (Br$_2$/CF$_3$CH$_3$) ranges 0.2 to 0.8, preferably 0.3 to 0.6, respectively in molar ratio. The molar ratio, Cl$_2$/Br$_2$ are not more than 1 and preferably ranges 0.05 to 0.6. When the reaction reagents pass through a reactor, their rates of passing through the reactor are proper to range 1 to 10 m/min. as a value calculated under the standard state.

Examples of the carboxylic acid salt, dicarboxylic acid salt, dicarboxylic acid salt having an ether-bonding and hydroxycarboxylic acid salt, which are not limitative are potassium acetate, sodium acetate, potassium benzoate, sodium benzoate, potassium γ-hydroxybutyrate, sodium γ-hydroxybutyrate, a potassium or sodium salt of bis-(3-carboxypropyl)ether, a potassium or sodium salt of oxalates and the like. These can be used in a mixture of at least two members.

Furthermore, when a MOOC(CH$_2$)$_3$O(CH$_2$)$_3$COOM', which is a class of the above-stated general formula MOOCR'OR"COOM' is used, a reaction product prepared by reacting γ-butyrolactone with an alkaline substance such as NaOH can be served without further treatment for the reaction. In addition, these hydrolysis reagents can be compounds containing water of crystallization.

The reaction temperature of this reaction is not lower than 130° C. and not higher than 250° C., preferably not lower than 140° C. and not higher than 230° C. In a case in which the reaction temperature is lower than the temperature range, the reaction rate becomes slower to result in a considerably long reaction time. On the contrary, the reaction temperature higher than the temperature range is not practical, because it causes a decrease of the object substance in yield due to side-reactions, degradation of the solvent, occurrence of corrosion of the reaction vessel and so on. The initial pressure may be of atmospheric one at the initiation of the reaction and the reaction can be carried out in these conditions because the self-generated pressure rises by the heating of raw materials and product substances. The hydrolysis can be also carried out under a pressurized condition attained by an inert gas such as nitrogen which does not affect the reaction so as to give a pressure higher than the self-generated one but not higher than 40 Kg/cm$^2$G at room temperature before the initiation of the reaction.

The molar ratio of γ-butyrolactone/1,1,1-trifluoro-2-halogenated ethane is not less than 0.5 and not more than 20, preferably not less than 0.8 and not more than 15. The molar ratio less than 0.5 is not economical because, in such a case the conversion of the 1,1,1-trifluoro-2-halogenated ethane decreases to cause increasing amounts of unreacted components to be recovered, a decrease in yield due to occurrence of side-reactions. On the other hand, the molar ratio more than 20 is not economical, because it is necessary to recover a large amount of γ-butyrolactone in such a case.

The carboxylic acid salt, dicarboxylic acid salt, dicarboxylic acid salt having an ether-bonding in molecule and alkaline substances may be in an amount not less than 0.25 mol. and not more than 10 mol., and preferably not less than 0.5 mol. and not more than 5 mols. based on the molarity of the 1,1,1-trifluoro-2-halogenated ethane.

When the carboxylic acid salt and dicarboxylic acid salt are used, the reaction proceeds in the absence of water but differs from in the above-stated(e) case of the hydroxycarboxylic acid ester and is mainly constituted a reaction to produce a 2,2,2-trifluoroethylcarboxylic acid ester. Therefore it is necessary to further carry out a hydrolysis reaction in order to obtain the object substance.

On the contrary, the conversion of CF$_3$CH$_2$X is remarkably reduced in the presence of water in an amount exceeding the necessary amount of water and the corrosion was remarkably promoted. Therefore, the amount of water to be added is not less than 0.5 and not more than 15, more preferably not less than 0.5 and not more than 4. When water of crystallization is contained in the carboxylic acid salts to be used in the reaction, then the amounts of the water of crystallization are estimated as a part of the above calculation of water amounts.

The reason why 2,2,2-trifluoroethanol is produced in a step without addition of water in the above-stated(e) case of the hydroxycarboxylic acid salts seems that the reaction follows the below-described reaction-equation which is exemplified by a salt of γ-hydroxybutyric acid.

CF$_3$CH$_2$Cl (or CF$_3$CH$_2$Br) + HOCH$_2$CH$_2$CH$_2$COOK

CF$_3$CH$_2$OCCH$_2$CH$_2$CH$_2$OH + KCl (or KBr)
       ‖
       O

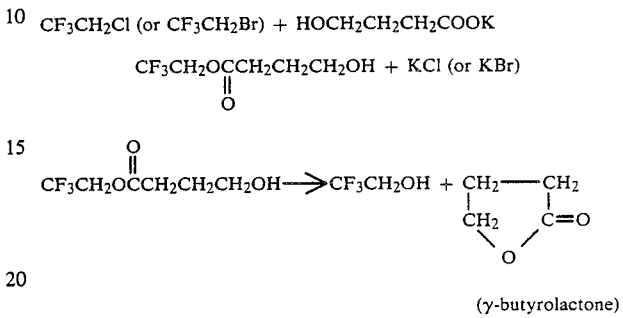

(γ-butyrolactone)

The reaction products can be separated to recover by a distillation after they are separated from unreacted carboxylic acid salts and a chloride or bromide of Na, K and Mg, and after 2,2,2-trifluorocarboxylic acid esters are saponified in a case in which they are produced though in small amounts.

Pressure vessels made of structural materials, for example, SUS304, SUS316, Inconel, nickel, chromium and Hastelloy can be used in the reaction but the structural materials are not restricted to them.

EXAMPLE 1

The raw material, CF$_3$CH$_2$Br was prepared as follows.

A reaction tube made of nickel and having the length of 80 cm and diameter of 1 inch was heated in an electric furnace to maintain its 50 cm part at the predetermined temperature of 600° C.

A raw material of CF$_3$CH$_3$ in an amount of 5.37 mol/hour was bubbled in a Br$_2$ liquid from a gas cylinder through gas flow meter to accompany with 3.17 mols./h of Br$_2$ gas and 0.75 mol/h of Cl$_2$ gas was further incorporated into the resulting mixture gas at the entrance of the reaction tube, which mixture gas was then introduced into the reaction tube. The passing rate of the reaction gas was 6.8 m/min in the reaction tube.

The reaction gas was cooled in a cooler through which brine was circulated, to liquefy it in a first collector and uncondensed gas was collected in a second collector which was cooled by dry ice-methanol.

These collected components was distilled to give CF$_3$CH$_2$Br, after they were washed with a cold 10% solution of NaOH.

Following to this, predetermined amounts of γ-butyrolactone, water and potassium acetate were charged into a 200 ml capacity of autoclave made of a structural material of SUS304, which was provided with a magnetic stirrer and the autoclave was sealed. The system was aspirated by vacuum and the above-stated CF$_3$CH$_2$Br which was previously gathered in a glass pressure vessel was introduced into the autoclave through a conduct pipe. After that, the content of the autoclave was pressurized by air to 2 Kg/cm$^2$G and heated to 150° C. in an electric furnace with stirring to react them for 4 hours. After completion of the reaction, gas components released from the autoclave were collected in a trap cooled by a dry ice-methanol. Subsequently, the autoclave was opened and the reaction solution was recovered by n-propanol used as a washing solvent which was previously cooled to 0° C. Crystalls of unreacted potassium acetate and produced potassium bromide were repeatedly washed with the washing solvent. The recovered gas components and reaction solution was analyzed and determined by the gas chromatography using methylisobutylketone as a internal standard substance.

Used amounts of the raw materials and recovered amounts of the reaction products and unreacted raw materials are shown in Table 1.

COMPARATIVE EXAMPLE 1

The reaction was carried out in the same manner as in Example 1 except for excluding to add water.

The water content of $\gamma$-butyrolactone used in this Comparative Example was determined by the Karl-Fisher method to give 0.1% by weight.

Results are shown in Table 1.

EXAMPLE 2

The reaction was carried out in the same manner as in Example 1 except for using $CF_3CH_2Cl$ as a raw material and adopting the reaction temperature of 200° C.

Results are shown in Table 1.

EXAMPLE 3

The reaction was carried out in the same manner as in Example 1 except for using $CH_3COONa.3H_2O$ as the carboxylic acid salt and adopting the reaction temperature of 170° C.

Results are shown in Table 1.

EXAMPLE 4

The reaction was carried out in the same manner as in Example 1 except for using $CF_3CH_2Cl$ as a raw material and $CH_3COONa.3H_2O$ as the carboxylic acid salt and adopting the reaction temperature of 220° C.

Results are shown in Table 1.

EXAMPLE 5

$CF_3CH_2Cl$ and $K_2CO_3$ were used as a raw material and the alkalline substance, respectively. The reaction was carried out at the reaction temperature of 200° C. after the raw materials was charged into the reaction vessel followed by the pressurization with $N_2$ to give a pressure of 4 Kg/cm$^2$G. The other conditions were the same as in Example 1.

Results are shown in Table 1.

EXAMPLE 6

The reaction was carried out in the same manner as in Example 5 except for using $Na_2CO_3$ as the alkalline substance.

Results are shown in Table 1.

EXAMPLE 7

The reaction was carried out in the same manner as in Example 5 except for using a mixture of 20 m mols. of $Na_2CO_3$ and 100 m mols. of $K_2CO_3$.

Results are shown in Table 1.

EXAMPLE 8

The reaction was carried out in the same manner as in Example 5 except for using KOH as the alkalline substance and adopting the reaction temperature of 225° C. and the reaction time of 2.5 hours.

Results are shown in Table 1.

EXAMPLE 9

The reaction was carried out in the same manner as in Example 5 except for using NaOH as the alkalline substance and adopting the reaction temperature of 225° C. and the reaction time of 6 hours.

Results are shown in Table 1.

EXAMPLE 10

The reaction was carried out in the same manner as in Example 5 except for using potassium benzoate as the carboxylic acid salt.

Results are shown in Table 1.

EXAMPLE 11

The reaction was carried out in the same manner as in Example 5 except for using potassium phthalate as the dicarboxylic acid salt and adopting the reaction temperature of 225° C.

Results are shown in Table 1.

EXAMPLE 12

The reaction was carried out in the same manner as in Example 5 except for using $KOOCCH_2CH_2COOK.3H_2O$ (potassium succinate) as the dicarboxylic acid salt.

EXAMPLE 13

The reaction was carried out in the same manner as in Example 5 except for using a mixture of 57.1 m mol. of $HO(CH_2)_3COOK$ (potassium $\gamma$-hydroxybutyrate) as the hydroxycarboxylic acid salt and 107 m mol. of $O[(CH_2)_3COOK]_2$ (a potassium salt of bis-(3-carboxypropyl)ether) as the dicarboxylic acid salt having an ether-bonding in molecule.

Results are shown in Table 1.

EXAMPLE 14

The reaction was carried out in the same manner as in Example 5 except for using $HO(CH_2)_3COOK$ (potassium $\gamma$-hydroxybutyrate) as the hydroxycarboxylic acid salt.

Results are shown in Table 1.

EXAMPLE 15

The reaction was carried out in the same manner as in Example 5 except for using $CH_3(CH_2)_2COOK$ (potassium butyrate) as the carboxylic acid salt.

Results are shown in Table 1.

EXAMPLE 16

The reaction was carried out in the same manner as in Example 5 except for using $CH_3CH=CHCOOK$ (potassium crotonate) as the carboxylic acid.

Results are shown in Table 1.

EXAMPLE 17

The reaction was carried out in the same manner as in Example 5 except for using $HOCH_2COOK$ (potassium glycolate) as the hydrocarboxylic acid salt.

Results are shown in Table 1.

EXAMPLE 18

The reaction was carried out in the same manner as in Example 5 except for using $CH_3(CH_2)_7CH=CH(CH_2)_7COOK$ (potassium oleate)

as the carboxylic acid salt, excluding the pressurization by nitrogen and conducting the reaction at a reaction temperature of 225° C. for 3 hours.

Results are shown in Table 1.

EXAMPLE 19

Predetermined amounts of γ-butyrolactone and potassium γ-hydroxybutyrate were charged into a 200 ml capacity autoclave made of a structural material of SUS304, which was provided with a magnetic stirrer and the autoclave was sealed. Vacuum was applied to the system and $CF_3CH_2Cl$ which was previously gathered in a glass pressure vessel was introduced into the autoclave through a conduct pipe. After that, the content of the autoclave was pressurized by nitrogen to 4 $Kg/cm^2G$ and heated to 200° C. in an electric furnace to react them for 4 hours.

After the completion of the reaction, gas components released from the autoclave were collected in a trap cooled by a dry ice-methanol. Subsequently, the autoclave was opened and the content was quickly filtered by a glass-filter to separate unreacted potassium γ-hydroxybutyrate and the produced potassium chloride from the reaction solution. The collected potassium γ-hydoxybutyrate and potassium chloride were repeatedly washed with γ-butyrolactone and incorporated with the washing solution.

The gas components and the reaction liquor recovered in these procedures were determined by the gas chromatography using dioxane as an internal standard substance.

Results are shown in Table 2.

EXAMPLE 20

Potassium γ-hydroxybutyrate was produced by a reaction of γ-butyrolactone and KOH in an autoclave and served for the reaction.

That is, predetermined amounts of γ-butyrolactone and solid potassium hydroxide having a water content of 13% by weight were charged into an autoclave. They were heated at 180° C. with stirring to react for 1 hours and then dehydrated by distillating water under vacuum. The distillate was analysed by the gas chromatography to determine the amount of γ-butyrolactone which was accompanied with water and after the autoclave was cooled to room temperature the contents remaining in the autoclave were gathered and were analyzed by HLC to determine potassium γ-hydroxybutyrate.

Then, in the same manner as in Example 19, $CF_3CH_2Cl$ was introduced into the autoclave to react and analyze. However, the pressurization by nitrogen after the introduction of $CF_3CH_2Cl$ was excluded.

EXAMPLE 21

Example 19 was repeated except for using $CF_3CH_2Br$ as a raw material and adopting a reaction temperature of 150° C.

Results are shown in Table 2.

TABLE 1

| | | Example 1 | Comparative Example 1 | Example 2 | Example 3 | Example 4 | Example 5 | Example 6 |
|---|---|---|---|---|---|---|---|---|
| Charged Amount of Raw Material (m mol) | Reagent for hydrolysis | $CH_3COOK$ 200 | $CH_3COOK$ 200 | $CH_3COOK$ 480 | $CH_3COONa$ $.3H_2O$ 118 | $CH_3COONa$ $.3H_2O$ 118 | $K_2CO_3$ 170 | $Na_2CO_3$ 100 |
| | $CF_3CH_2Br$ | 112 | 114 | — | 118 | — | — | — |
| | $CF_3CH_2Cl$ | — | — | 214 | — | 115 | 336 | 105 |
| | $H_2O$ | 200 | — | 477 | — | — | 340 | 200 |
| | γ-butyrolactone | 1569 | 1569 | 833 | 1569 | — | 1050 | 1394 |
| Recovered Amount (m mol.) | Unreacted $CF_3CH_2Br$ | 17.6 | 4.6 | — | 15.2 | — | — | — |
| | Unreacted $CF_3CH_2Cl$ | — | — | 51.4 | — | 12.4 | 148 | 65.9 |
| | $CF_3CH_2OCOR$ | R; $CH_3$— 4.3 | R; $CH_3$— 77.2 | R; $CH_3$— 1.0 | R; $CH_3$— 2.3 | R; $CH_3$— 1.0 | — | — |
| | $CF_3CH_2OH$ | 82.5 | 16.3 | 142 | 85.3 | 89.2 | 173 | 40.1 |
| Reaction Condition | Reaction Temperature (°C.) | 150 | 150 | 200 | 170 | 220 | 200 | 200 |
| | Reaction Time (hrs) | 4 | 4 | 4 | 4 | 4 | 4 | 4 |

| | | Example 7 | Example 8 | Example 9 | Example 10 | Example 11 | Example 12 | Example 13 |
|---|---|---|---|---|---|---|---|---|
| Charged Amount of Raw Material (m mol) | Reagent for hydrolysis | $Na_2CO_3$ 20 $K_2CO_3$ 100 | KOH 200 | NaOH 200 |  200 |  200 | $CH_2COOK$ \| $CH_2COOK$ $.3H_2O$ 155 | $HO(CH_2)_3CO_2K$ 57.1 $O[(CH_2)_3CO_2K]_2$ 107 |
| | $CF_3CH_2Br$ | — | — | — | — | — | — | — |
| | $CF_3CH_2Cl$ | 196 | 214 | 215 | 197 | 198 | 197 | 199 |
| | $H_2O$ | 160 | 200 | 200 | 200 | 200 | 671 | 1538 |
| | γ-butyrolactone | 1390 | 1394 | 1394 | 1400 | 1394 | 1394 | 1393 |
| Recovered Amount (m mol.) | Unreacted $CF_3CH_2Br$ | — | — | — | — | — | — | — |
| | Unreacted $CF_3CH_2Cl$ | 43.8 | 29.9 | 67.7 | 10.2 | 53.2 | 133 | 53.4 |
| | $CF_3CH_2OCOR$ | — | — | — | — | — | — | — |
| | $CF_3CH_2OH$ | 140 | 165 | 140 | 106 | 116 | 64.3 | 134 |
| Reaction Condition | Reaction Temperature (°C.) | 200 | 225 | 225 | 200 | 225 | 200 | 200 |
| | Reaction Time (hrs) | 4 | 2.5 | 6 | 4 | 4 | 4 | 4 |

TABLE 1-continued

| | | Example 14 | Example 15 | Example 16 | Example 17 | Example 18 |
|---|---|---|---|---|---|---|
| Charged Amount of Raw Material (m mol.) | Reagent for hydrolysis | $HO(CH_2)_3CO_2K$ 200 | $CH_3(CH_2)_2CO_2K$ 200 | $CH_3CH=CHCO_2K$ 200 | $HOCH_2CO_2K$ 200 | $C_{17}H_{33}COOK$ 120 |
| | $CF_3CH_2Br$ | — | — | — | — | — |
| | $CF_3CH_2Cl$ | 202 | 207 | 198 | 201 | 120 |
| | $H_2O$ | 201 | 200 | 199 | 204 | 202 |
| | γ-butyrolactone | 1394 | 1394 | 1393 | 1394 | 1394 |
| Recovered Amount (m mol.) | Unreacted $CF_3CH_2Br$ | — | — | — | — | — |
| | Unreacted $CF_3CH_2Cl$ | 38.8 | 40.6 | | 124 | 12.0 |
| | $CF_3CH_2OCOR$ | | R; $CH_3(CH_2)_2$— 20.9 | R; $CH_3CH=CH$— 16.0 | | |
| | $CF_3CH_2OH$ | 130 | 122 | 117 | 65.5 | 78.0 |
| Reaction Condition | Reaction Temperature (°C.) | 200 | 200 | 200 | 200 | 225 |
| | Reaction Time (hrs.) | 4 | 4 | 4 | 4 | 3 |

TABLE 2

| | | Example 19 | Example 20 | Example 21 |
|---|---|---|---|---|
| Charged Amount of Raw Material (m mol.) | γ-Hydroxy butyrate | Potassium Salt 200 | Potassium Salt 192 | Sodium Salt 120 Potassium Salt 80 (Produced by the reaction of 220 m mol. of KOH) |
| | $CF_3CH_2Br$ | | | 205 |
| | $CF_3CH_2Cl$ | 201 | 214 | |
| | γ-Butyrolactone | 1394 | 1394 | 1396 |
| Recovered Amount (m mol.) | Unreacted $CF_3CH_2Br$ | | | 91.2 |
| | Unreacted $CF_3CH_2Cl$ | 33.3 | 42.6 | |
| | $CF_3CH_2OH$ | 123 | 137 | 98.7 |
| Reaction Condition | Reaction Temperature (°C.) | 200 | 200 | 150 |
| | Reaction Time (hrs) | 4 | 4 | 4 |

We claim:

1. A process for producing 2,2,2-trifluoroethanol, which comprises reacting an 1,1,1-trifluoro-2-halogenated ethane in γ-butyrolactone used as a solvent in the presence of at least one of the following reagent systems (a) to (e):

(a) water and at least one carboxylic acid salt represented by the general formula

RCOOM wherein R is an alkyl group or a hydroxyalkyl group, each of which has a carbon number of not more than 19, or phenyl group, and M is Na, K, or Mg;

(b) water and at least one dicarboxylic acid salt represented by the general formula

MOOCR'COOM' wherein R' is an alkylene group, having a carbon number of 0 to 8, or phenylene group, and M and M' are Na, K or Mg, which can be identical or different from each other;

(c) water and at least one dicarboxylic acid salt having an ether-bonding in molecule, which is represented by the general formula

MOOCR'OR"COOM' where R' and R" are alkylene groups having a summed up carbon number of not more than 10, which can be identical to or different from each other, and M and M' are Na, K or Mg, which can be identical to different from each other;

(d) water and at least one alkaline substance consisting of NaOH, KOH, $Na_2CO_3$, $K_2CO_3$, $NaHCO_3$ and $KHCO_3$; and (e) at least one hydroxycarboxylic acid salt represented by the formula

R'''COOM wherein R''' is a hydroxyalkyl group having a carbon number of not more than 5, and M is Na, K or Mg, wherein the molar ratio of γ-butyrolactone to the 1,1,1-trifluoro-2-halogenated ethane is 0.5 to 20, wherein further the molar ratio of any one of the carboxylic acid salt, the dicarboxylic acid salt, the dicarboxylic acid salt having an ether-bonding in molecule, the alkaline substance and the hydrocarboxylic acid salt to 1,1,1-trifluoro-2-halogenated ethane is 0.25 to 10, wherein also the molar ratio of water to 1,1,1-trifluoro-2-halogenated ethane is 0.5 to 15, and wherein the reaction temperature is 130° to 250° C., the 1,1,1-trifluoro-2-halogenated ethane being selected from the group consisting of 1,1,1-trifluoro-2-bromoethane and 1,1,1-trifluoro-2-chloroethane, in the presence of at least the self-generated pressure corresponding to the reaction temperature.

2. The process for producing 2,2,2-trifluoroethanol as set forth in claim 1, wherein 1,1,1-trifluoro-2-bromoethane is produced by reacting 1,1,1-trifluoroethane and bromine in the presence of chlorine.

3. The process for producing 2,2,2-trifluoroethanol as set forth in any one of claims 1 and 2, wherein the carboxylic acid salt is an acetate.

4. The process for producing 2,2,2-trifluoroethanol as set forth in claim 1, wherein the hydroxycarboxylic acid salt is a hydroxybutyrate.

5. The process for producing 2,2,2-trifluoroethanol as set forth in claim 3, wherein the reagent system is water and Na, K or Mg acetate.

6. The process for producing 2,2,2-trifluoroethanol as set forth in claim 4, wherein the reagent system is a Na, K or Mg hydroxybutyrate.

* * * * *